United States Patent [19]

Furrer et al.

[11] 4,207,321

[45] Jun. 10, 1980

[54] PHARMACEUTICAL COMPOSITIONS CONTAINING XANTHINES

[75] Inventors: Harald Furrer, Kelkheim; Alfons Söder, Frankfurt am Main-Schwanheim; Jaromir Komarek, Wiesbaden; Heinz-Joachim Hinze, Wiesbaden-Auringen; Gerhard Münch, Bad-Schwalbach, all of Fed. Rep. of Germany

[73] Assignee: Hoechst Aktiengesellschaft, Frankfurt, Fed. Rep. of Germany

[21] Appl. No.: 947,508

[22] Filed: Oct. 2, 1978

Related U.S. Application Data

[63] Continuation-in-part of Ser. No. 883,052, Mar. 3, 1978, abandoned.

[30] Foreign Application Priority Data

Apr. 2, 1977 [DE] Fed. Rep. of Germany ....... 2714953

[51] Int. Cl.² ............................................. C07D 473/12
[52] U.S. Cl. ..................................... 424/253; 544/267; 544/273
[58] Field of Search ................. 544/273, 267; 424/253

[56] References Cited

U.S. PATENT DOCUMENTS

| | | | |
|---|---|---|---|
| 2,731,465 | 1/1956 | Schroeder | 544/267 |
| 3,864,469 | 2/1975 | Reiser et al. | 424/253 |
| 4,089,959 | 5/1978 | Diamond | 424/253 |
| 4,108,995 | 8/1978 | Mohler et al. | 424/253 |

FOREIGN PATENT DOCUMENTS

| | | |
|---|---|---|
| 2432702 | 1/1976 | Fed. Rep. of Germany . |
| 97979 | 10/1921 | Switzerland . |
| 365211 | 1/1932 | United Kingdom . |

OTHER PUBLICATIONS

Gemmill, CA 42, 985f, g (1947).
McColl et al., CA 51, 4553e (1956).
Ionica, CA 71, 872b (1967).

*Primary Examiner*—Nicholas S. Rizzo
*Attorney, Agent, or Firm*—Berman, Aisenberg & Platt

[57] ABSTRACT

A pharmaceutical composition having as an essential ingredient a compound of the formula

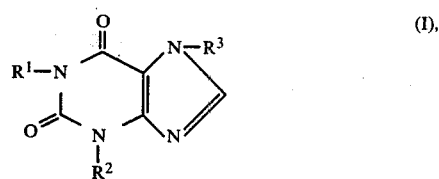

wherein one to three of $R^1$, $R^2$ and $R^3$ represent an alkenyl group having from 4 to 8 carbon atoms, the other ones are alkyl having from 1 to 12 carbon atoms, and $R^1$ may also be hydrogen, the compounds themselves and a process for preparing them.

21 Claims, No Drawings

PHARMACEUTICAL COMPOSITIONS CONTAINING XANTHINES

This application is a continuation-in-part of copending application Ser. No. 883,052 filed Mar. 3, 1978.

A process for the hydration of (Ω-1)-alkenyl-xanthine derivatives of general formula

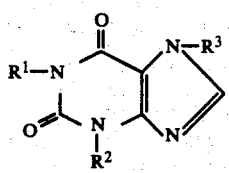

in the presence of a catalyst to form corresponding (Ω-1)-hydroxy-alkyl-xanthines is known. In this formula one of $R^1$, $R^2$ and $R^3$ represents an (Ω-1)-alkenyl group having from 4 to 8 carbon atoms and being unbranched in (Ω-1)-position; the two other of $R^1$, $R^2$ and $R^3$ represent straight-chained or branched alkyl groups having from 1 to 12 carbon atoms; $R^1$ and/or $R^3$ may also represent hydrogen atoms and at least one of $R^1$, $R^2$ and $R^3$ has at least 5 carbon atoms. The (Ω-1)-hydroxy-alkylxanthines are suitable as pharmaceuticals, especially for promoting cerebral blood flow.

It is also known from U.S. Pat. No. 3,864,469 to produce a pharmaceutical preparation exhibiting delayed release of an active substance which comprises
a. intimately mixing at least two therapeutically-active substances, at least one of which is more rapidly absorbable than another and at least one of which is in a non-solid state, each other therapeutically-active substance being homogeneously incorporated into any such substance in a non-solid state;
b. solidifying the resulting mixture and
c. forming the solidified admixture into a solid pharmaceutical preparation.

This process is said to be particularly suitable for the joint processing of nicotinic acid (pyridine-3-carboxylic acid) and/or its therapeutically active derivatives, such as salts, esters or amides, and/or suitably substituted xanthines, which are substituted in the 1-, 3- or 7-position by a hydrocarbon group with 2 or 3 to 20 C-atoms bound at an acyclic carbon atom, and are substituted in both the other stated positions with an alkyl group with 1 or 2 C-atoms, preferably a methyl group. The products obtained are stated to exhibit, due to the specific processing conditions, either delayed release of a therapeutically-active substance or to effect stabilization of vitamins. Suitable groups are substituted or unsubstituted straight- or branched-chain, saturated or mono- or poly-olefinically unsaturated hydrocarbon groups with from 2 or 3 to 20 carbon atoms; the unsubstituted hydrocarbon groups preferably have from 3 to 15 carbon atoms.

Specific mono- and poly-olefinically unsaturated groups referred to are $\Delta^1$- and $\Delta^2$-pentenyl, $\Delta^3$-octenyl, octadecen-9-yl, octadecadien-9,12-yl and octadecatrien-9,12,15-yl. No further disclosure with regard to the combination of these compounds with nicotinic acid and/or its therapeutically active derivatives is made in addition to the foregoing statement, and no indication is presented of therapeutic properties which the xanthines containing a mono- or poly-olefinically unsaturated hydrocarbon substituent may have themselves. We have now found that the alkenyl-xanthines, and especially (Ω-1)-alkenyl-xanthines, are distinguished by an activity of promoting blood perfusion, especially in the cerebrovascular region.

According to the present invention there is provided a pharmaceutical composition comprising at least one compound of the said formula, wherein one to three of the groups $R^1$, $R^2$ and $R^3$ represent an alkenyl group having from 4 to 8 carbon atoms, which may be straight-chained or branched, in which the other radicals, if any, are straight-chained or branched alkyl groups having fromm 1 to 12 carbon atoms and in which $R^1$ may also be hydrogen. In the preferred compositions these compounds are the sole therapeutically active ingredient. Thus, a preferred embodiment of the invention consists in a substantially nontoxic pharmaceutical composition for increasing blood perfusion comprising carrier, diluent or excipient in addition to an effective concentration of active ingredient which consists essentially of substituted xanthine of formula I wherein each of $R^1$, $R^2$ and $R^3$ has one of the meanings indicated before. In the aforementioned compositions those compounds of formula I are preferred which contain at least one (Ω-1)-alkenyl group. The compositions of the invention may also contain compounds of formula (I) in which one of $R^1$, $R^2$ and $R^3$ is an (Ω-1)-alkenyl with 4 to 8 carbon atoms in which the carbon atom bearing the double bond is separated from the xanthine nucleus by at least one saturated carbon atom and both of the other groups are methyl, however, $R^1$ may also be a hydrogen atom, but $R^2$ always represents a methyl or an alkenyl group. One of $R^1$, $R^2$ and $R^3$, and particularly one of $R^1$ and $R^3$ is preferably a straight-chained (Ω-1)-alkenyl, particularly when $R^2$ is methyl. In more generic terms, the (Ω-1)alkenyl has at any rate a chain of at least 4 carbon atoms. In a more preferred embodiment, the alkenyl has 5 to 8 carbon atoms. Preferred compositions contain compounds wherein only one of $R^1$, $R^2$ and $R^3$ is an alkyl having at most 2 carbon atoms and the other ones are alkenyl, alkyl having at least 3 carbon atoms or wherein $R^1$ is hydrogen.

According to a further feature of the invention there are provided novel alkenyl xanthines of formula (I), wherein $R^1$, $R^2$ and $R^3$ represents the groups indicated above, but altogether have a meaning other than a 1-(but-3-enyl), 1-(pent-4-enyl), 1-(hex-5-enyl), 1-(2-methyl-but-3-enyl) group when $R^2$ and $R^3$ both represent methyl groups; or other than a hex-5-enyl group when $R^2$ represents a methyl group and $R^3$ represents an ethyl, propyl, butyl, isobutyl or decyl group; or other than 1,3-dimethyl-7-(2-methyl-but-3-enyl), -7-(but-3-enyl), -7-(pent-4-enyl), -7-(hex-5-enyl) or -7-(hept-6-enyl)or 3-methyl-7-(hex-5-enyl) (i.e. wherein $R^1$ is a hydrogen atom), or 1-propyl-, 1-isobutyl-, 1-pentyl-, 1-hexyl-3-methyl-7-(hex-5-enyl) or 1,7-di-(hex-5-enyl)-3-methyl.

Other suitable compounds are those in which one to three of $R^1$, $R^2$ and $R^3$ represent an alkenyl group having from 4 to 8 carbon atoms, others are alkyl having from 1 to 12 carbon atoms or $R^1$ is optionally hydrogen. When $R^2$ is methyl and $R^1$ or $R^3$ is an (Ω-1) alkenyl group unbranched in the (Ω-1-)-position, the sum of the carbon atoms of the alkyl substituents $R^1$ and $R^2$ is, however, more than 7 and the sum of the carbon atoms of the alkyl substituents $R^2$ and $R^3$ is more than 11.

Special embodiments of the invention comprise those compounds in which at least one of $R^1$, $R^2$ and $R^3$ represents an alkyl group having from 2 to 12, and particularly from 3 to 12 carbon atoms, and at least one represents a butenyl or pentenyl group, $R^1$ being said alkyl, alkenyl or even hydrogen and one of $R^1$, $R^2$ and $R^3$ optionally being methyl. Also especially preferred are compounds in which more than one of the groups $R^1$, $R^2$ and $R^3$ are alkenyl groups; in the preferred of these compounds the double bond is in the ($\Omega$-1)-position. Another particular embodiment relates to hexenyl compounds in which the double bond is in a position other than the ($\Omega$-1)-position. Other particular embodiments relate to the following groups of compounds: Compounds, wherein $R^2$ is alkyl having from 2 to 12 carbon atoms or alkenyl having from 4 to 8 carbon atoms and wherein only one of $R^1$, $R^2$ and $R^3$ is alkyl having at most 2 carbon atoms and the other ones are alkenyl, alkyl having at least three carbon atoms or $R^1$ optionally is hydrogen; compounds, wherein $R^1$ is hydrogen, $R^2$ is alkyl having from 1 to 12 carbon atoms and $R^3$ is butenyl or pentenyl; compounds, wherein the alkenyl is branched and has a chain length of at least 4, preferably 6 carbon atoms; compounds, wherein $R^1$ is ethyl, $R^2$ is methyl or ethyl and $R^3$ is alkenyl; compounds, wherein $R^1$ is alkenyl, $R^2$ is methyl and $R^3$ is hexyl; compounds, wherein $R^1$ is alkyl having from 2 to 12 carbon atoms or alkenyl, $R^2$ is alkyl having from 2 to 12 carbon atoms and $R^3$ is alkyl having from 1 to 12 carbon atoms or alkenyl with the proviso that one of the groups $R^1$ and $R^3$ is alkenyl, at least one of the groups $R^1$ and $R^2$ has at least 3 carbon atoms and all of $R^1$, $R^2$ and $R^3$ have not the same number of carbon atoms.

Another object of the invention consists in processes for the preparation of the novel alkenyl-xanthines. These are prepared according to one process by reacting a corresponding xanthine in which however at least one of $R^1$, $R^2$ and $R^3$ is hydrogen and up to two of these groups are an alkyl and/or alkenyl group, optionally in the presence of a base or in the form of their salts, with a compound of the formula R-X [in which X represents a halogen, preferably chlorine or bromine, or a sulphonic acid ester group or phosphoric acid ester group, and R represents an alkenyl group having from 4 to 8 carbon atoms (for the introduction of alkenyl groups) or an alkyl group having from 1 to 12 carbon atoms (for the introduction of an alkyl group)]. Thus, unsubstituted xanthine; or 1-, 3- or 7-monoalkylxanthines or monoalkenyl-xanthines; or 1,3-, 1,7- or 3,7-dialkyl- or dialkenyl-xanthines or a corresponding monoalkyl-monoalkenyl-xanthine are reacted. The alkyl and alkenyl groups may be straight-chained or branched.

The xanthine derivatives used in this process are preferably in the form of their alkali metal or alkaline-earth metal salts.

This process may be carried out in a conventional manner, generally at a temperature of from 20° to 160° C., preferably from 35 to 125° C., and optionally at an elevated or reduced pressure, but usually at atmospheric pressure. The individual starting materials may be used in stoichiometric or, for economic reasons, in nonstoichiometric quantities. The reaction time is, of course, generally dependent on the temperature. The reactions may already be completed after one hour, although the reaction time generally amounts to more than 6 hours.

The reactions are conveniently effected in the presence of inorganic or organic basic compounds, such as an alkali metal or alkaline earth metal hydroxide, carbonate, hydride or alcoholate, or of an organic base such as triethylamine or tributylamine. Alkali metal or alkaline-earth metal salts of the xanthines are advantageously produced in situ.

The above processes are conveniently effected in a solvent. Convenient solvents are those which are miscible with water, a part of them in admixture with water, e.g. methanol, ethanol, propanol, isopropanol, the various butanols, acetone, pyridine, polyhydric alcohols such as ethylene glycol and ethylene glycol monomethyl or ethyl ether, aprotic dipolar solvents such as formamide, dimethylformamide, dimethylacetamide, N-methylpyrrolidone, tetramethyl-urea, hexamethylphosphoric acid trisamide and dimethylsulphoxide. Hydrocarbons such as benzene, toluene or xylene, as well as mixtures of the said solvents, if they are mutually miscible, may also be used.

This process enables the same or different alkenyl and/or alkyl substituents to be introduced in succession or several substituents of the same kind can be linked to the xanthine nucleus without isolating any intermediate product in a one batch reaction. The new alkenyl xanthines may also be prepared from xanthines containing oxoalkyl or hydroxyalkyl side-groups by (a) reacting oxoalkyl-xanthines with olefinishing agents, whereby the number of carbon atoms in the oxoalkyl group and in the group introduced with the olefinising agent is in total from 4 to 8 carbon atoms; or (b) dehydrating hydroxyalkyl-xanthines in which the hydroxyalkyl group has from 4 to 8 carbon atoms.

Process (a) may be effected by the known olefinising reactions, for example, according to Wittig-Horner (Houben-Weyl, volume 5/1 b (1972) 383 et seq.) Oxoalkyl-xanthines may be converted into corresponding alkenyl-xanthines in solvents such as dioxan, dimethylformamide or dimethylsulphoxide generally at temperatures of from 20° to 160° C., preferably of from 20° to 80° C., by reaction, for example, with phosphinyl alkylenes. Branch-chained xanthine derivatives may also be obtained by this process.

Dehydration of hydroxyalkyl-xanthines into alkenyl-xanthines may be carried out by known techniques, for example, in the presence of acid catalysts, e.g. p-toluenesulphonic acid.

If 1,3,7-trisubstituted-hydroxyalkyl-xanthines are used, the Tschugaeff xanthate method is advantageously adopted, i.e. by converting the hydroxyalkyl xanthines preferably in benzene, ether or toluene solution via their alkali metal salts, preferably their sodium salts, by reaction with carbon disulphide and methyl iodide into methyl xanthates which are transformed at temperatures of 110° to 230° C. into corresponding alkenyl-xanthines.

According to the process of the invention there may be prepared as well those alkenyl-xanthines in which the

groups is bound directly to a nitrogen atom as those in which the

grouping is separated by at least one, preferably 2 to 6 carbon atoms from the xanthine nucleus.

In formula I each alkenyl group of $R^1$, $R^2$ and/or $R^3$ may be, for example, butenyl, pentenyl, hexenyl, heptenyl, octenyl, as well as their isomers or their lower alkyl-substituted derivatives having from 4 to 8 carbon atoms, particularly those in which the alkyl substituent has up to two carbon atoms, such as methallyl, methylcrotyl, methylpentenyl, methylhexenyl, methylheptenyl, ethylcrotyl, ethylpentenyl and ethylhexenyl. The alkyl radicals of $R^1$, $R^2$ and $R^3$ may for example be methyl, ethyl, n-propyl, isopropyl, n-butyl, iso-butyl or tert.-butyl, n- or iso-pentyl, n- or iso-hexyl, n- or iso-heptyl, n- or iso-octyl such as 2-ethylhexyl, n- or iso-nonyl, n- or iso-decyl and n- or iso-dodecyl.

Particular substances which may be contained in the pharmaceutical compositions according to the invention are in addition to those mentioned in the examples.
1-methyl-3-n-butyl-7-(oct-7-enyl)-xanthine;
3,7-di-(pent-4-enyl)-xanthine;
1,3,7-tri-(pent-4-enyl)-xanthine;
1-n-propyl-3-(hex-5-enyl)-7-n-hexyl-xanthine;
1-methyl-3-ethyl-7-(hept-6-enyl)-xanthine;
1,7-dimethyl-3-(pent-4-enyl)-xanthine;
1,3-di-(n-hexyl)-7-(but-3-enyl)-xanthine;
1,3-di-(n-butyl)-7-(hex-5-enyl)-xanthine;
1-(2-methyl-but-3-enyl)-3,7-dimethyl-xanthine;
1-(hex-5-enyl)-3-methyl-7-butyl and 7-isobutyl-xanthine;
1,3-di-methyl-7-(2-methyl-but-3-enyl)-xanthine;
1,3-dimethyl-7-(hept-6-enyl)-xanthine;
1-propyl-, 1-isobutyl-, and 1-pentyl-3-methyl-7-(hex-5-enyl)-xanthine; and
1,7-di-(hex-5-enyl)-3-methyl-xanthine.

The pharmaceutical compositions according to the invention have interesting therapeutic properties and may be administered orally or rectally, e.g. in solid or dissolved forms. Xanthine derivatives according to the invention which are readily soluble in water, may also be administered parenterally.

In the pharmaceutical compositions the xanthine derivatives of the invention may be used in combination with further therapeutically active compounds particularly with coronary active agents and with ergot alkoloids.

The formulation to the conventional forms of administration such as solutions, emulsions, tablets, coated tablets, microcapsules, suppositories and granulates, is conducted in conventional manner by using excipients conventional therefor, such as carriers; disintegrants; binders;, coatings; swelling, sliding or lubricating agents; flavourings; sweeteners; and solubilising agents. Suitable adjuvants are for example lactose, mannitol, talcum, milk protein, starch, gelatin, cellulose or its derivatives such as methyl cellulose, hydroxyethyl cellulose or suitable swelling or non-swelling copolymers. By the use of extenders, which can be used in lesser or greater amounts, the decomposition of the preparation and, as a result the release of the active ingredient may be influenced.

The pharmaceutical compositions may be presented in the form of injectible solutions of compounds of general formula I in sterile water, e.g. in double-distilled water. As indicated above they may also be in a solid dosage unit form. Each dosage unit may contain a defined amount of the active substance of formula I, viz. dependent on the degree of activity, from 10 to 1000 mg, generally up to 400 mg and especially up to 200 mg. Thus, the average quantity of the compounds of formula I administered is in the range of 0.2 to 20 mg per kg of body weight.

The dosage unit may be administered one or more times daily, the number of administrations depending on the content of active ingredient and on the type of administrations. More frequent administration is recommended if for example the dosage unit has only a small content of active substance; but if the content is relatively high, the composition may be administered only once a day. The length of time over which administration may be effected during treatment may range from one to several weeks, although the dosage units may be administered over two or more years.

The pharmaceutical compositions have in particular in activity of promoting blood perfusion at a low toxicity of the active ingredients which especially is shown by a strong increase of the cerebral blood perfusion.

INVESTIGATION OF THE CEREBRAL BLOOD PERFUSION IN CATS

A heat-conduction probe was used to measure local cerebral blood perfusion (in the cortex). The method necessary to measure heat conduction was adopted in detail from the experiments described by (1) Betz et al.: Pflügers Arch. ges. Physiol. 288, 389 (1966),
(2) Priebe, L. et al.: Pflügers Arch. ges. Physiol. 294, 3, 26 (1967),
(3) Betz, E.: Symposium der Dtsch. Ges. f. Angiologic, 6. Jahrestagung, Munich (1968),
(4) Betz, E.: Pflügers Arch. ges. Physiol. 284, 3, 278 (1965)
(5) Betz, E.: Acta Neurol. Scand., Suppl. 14, 29 (1965),
(6) Betz, E.: Physiological Rev. 52, 3 (1972).

The tests were conducted on anaesthetised cats (sodium pentobarbital 35 mg/kg body weight i.p.). Blood pressure was measured in a femoral artery using a Statham device. Table 1 indicates for some of the alkenyl-xanthines prepared, the duration of activity as a half-value time (HVT) and the intensity of activity as the difference in the heat-conduction number $\lambda$ ($\Delta\lambda = \lambda_{after} - \lambda_{before}$) in comparison with corresponding values for the vasotherapeutic product theophylline-ethylenediamine. The claimed substances are shown to have a superiority both in the intensity of the effect and in the duration of activity from fluvographic measurement of cerebral blood perfusion in cats.

Table 1

Activity of various alkenyl xanthines and theophylline-ethylenediamine on cerebral blood perfusion in cats.

| Substance | Dose in mg/kg i.v. | Change in blood perfusion $\Delta\lambda$ | HVT[min] |
|---|---|---|---|
| Example 1 | 2 | +3 | 0.5 |
| | 5 | +4.5 | 2 |
| Example 2 | 2 | +4.5 | 2 |
| | 5 | +4.2 | 4 |
| Example 3 | 2 | +2.2 | 10 |
| | 5 | +6 | 15 |
| Example 4 | 2 | +7.3 | 5 |
| | 5 | +7.5 | 3 |
| Example 5 | 2 | +3.3 | 1 |
| | 5 | +3.7 | 5 |

Table 1-continued

Activity of various alkenyl xanthines and theophylline-ethylene-diamine on cerebral blood perfusion in cats.

| Substance | Dose in mg/kg i.v. | Change in blood perfusion Δλ | HVT[min] |
|---|---|---|---|
| Theophylline-ethylene- | 1 | +0.19 | 1.8 |
| diamine | 2 | +0.15 | 1.8 |
| (Comparison) | 5 | +0.18 | 3.3 |
| | 10 | +0.53 | 1.7 |

In the following Examples the ratios relate to volume ratios.

EXAMPLES

1: 1,3-Dimethyl-7-(but-3-enyl)-xanthine 13.9 g of 4-bromo-but-1-ene are reacted with 20.2 g of sodium theophylline in 200 ml of dimethyl-formamide at 120° C. with stirring for approximately 6 to 8 hours until the reaction is complete as indicated by thin-layer chromatography. The solvent is then removed under reduced pressure. The residue is dissolved at 20° C. in 100 ml of methylene chloride, separated from insoluble sodium bromide and purified through a column packed with neutral aluminum oxide to remove small quantities of dark-coloured accompanying substances. Melting point: 110° C. (acetone); yield: 21.6 g (91% of theory relative to the starting material used). After thin-layer chromatography on Merck DC finished plates of silica gel 60 F$_{254}$ with benzene/acetone (6:4) as eluent, the product has an R$_f$ value of 0.54; and with nitromethane/benzene/pyridine (20:10:3) as eluent, an R$_f$ value of 0.65. Utra-violet light was used as indicator, the pyridine of the eluent having, however, to be removed at 50° C. under reduced pressure because of its property to extinguish fluorescence.

2 to 5: The following compounds are prepared analogously from the corresponding dimethyl compounds:
1,3-Dimethyl-7-(pent-4-enyl)-xanthine
1,3-Dimethyl-7-(hex-5-enyl)-xanthine
1-(But-3-enyl)-3,7-dimethyl-xanthine
1-(Pent-4-enyl)-3,7-dimethyl-xanthine The physical data of these compounds are set out in Table 2.

6: 1-(But-3-enyl)-3-methyl-7-n-propyl-xanthine 20.8 g of 3-methyl-7-propyl-xanthine, 13.8 g of anhydrous potassium carbonate and 13.5 g of 4-bromo-but-1-ene are refluxed for 8 hours in 150 ml of dimethyl-formamide, and the solvent is then removed under reduced pressure. The residue is then dissolved in 150 ml of 1 N sodium hydroxide solution and the alkaline solution is extracted with methylene chloride. The residue obtained after evaporation of the methylene chloride is triturated with 100 ml of diisopropyl ether and unreacted 3-methyl-7-propyl-xanthine is removed. 15.6 g (70% of theory relative to 3-methyl-7-propyl-xanthine consumed) of the title compound of melting point 48° C. (from n-hexane) are obtained from the filtrate.

7 to 10: The following compounds are prepared analogously to Example 6 from the corresponding dialkyl-xanthine compounds:
1-(But-3-enyl)-3-methyl-7-hexyl-xanthine
1-(Hex-5-enyl)-3-methyl-7-propyl-xanthine
1-(Hex-5-enyl)-3-methyl-7-hexyl-xanthine
1-(Hex-5-enyl)-3-methyl-7-decyl-xanthine The physical data of the compounds are set out in Table 2.

11: 1-Ethyl-3-methyl-7-(hex-5-enyl)-xanthine 20 g of 3-methyl-7-(hex-5-enyl)-xanthine (see Example 22) are added to a solution of approximately 3.3 g of NaOH in 70 ml of methanol/water (1:1) and 9 g of ethyl bromide are added thereto. The mixture is kept at 40° C. under a nitrogen atmosphere for 40 hours. The solvent is then removed under reduced pressure, the residue dissolved in diethyl ether and the pH of the solution is adjusted with aqueous sodium hydroxide solution to a pH-value of 13.5 to remove unreacted 3-methyl-7-(hex-5-enyl)-xanthine. 1-Ethyl-3-methyl-7-(hex-5-enyl)-xanthine recovered from the ether phase is subsequently subjected to column chromatography using silica gel with methylene chloride/acetone (8:2) as eluent followed by distillation under reduced pressure and is obtained as a colourless oil. Yield: 11.2 g (81.3% of theory relative to reacted starting material) of the title compound, $n_D^{20} = 1.5415$.

12: 1-Propyl-3-methyl-7-(but-3-enyl)-xanthine

The manufacture is carried out analogously to Example 11 from 3-methyl-7-(but-3-enyl)-xanthine (see Example 20), but with the difference that the reaction temperature is 70° C.

13 and 14: 1-Hexyl-3-methyl-7-(but-3-enyl)-xanthine and 1-hexyl-3-methyl-7-(pent-4-enyl)-xanthine are prepared analogously to Example 1.

15: 1-Decyl-3-methyl-7-(but-3-enyl)-xanthine is prepared analogously to Example 12.

16: 1-Methyl-3-ethyl-7-(hex-5-enyl)-xanthine is prepared analogously to Example 11 from 3-ethyl-7-(hex-5-enyl)-xanthine (see Example 24).

17: 1,3-Diethyl-7-(pent-4-enyl)-xanthine is prepared analogously to Example 12 from 1,3-diethyl-xanthine and 5-bromopent-1-ene; the yield relative to the starting material used is 84%.

18: 1,3-Diethyl-7-(hex-5-enyl)-xanthine is prepared analogously to Example 12 from 1,3-diethyl-xanthine; the yield relative to the starting material used in 79%.

19: 1,3-Di-n-butyl-7-(but-3-enyl)-xanthine 38.9 g of 1,3-di-n-butyl-xanthine are added at 25° C. to a solution of 3.4 g of sodium in 200 ml of absolute ethanol. 20.5 g of 4-bromobut-1-ene are then added at 50° C. After stirring for 46 hours under a nitrogen atmosphere at 70° C. the reaction mixture is cooled to 20° C., precipitated sodium bromide is filtered off and the filtrate is then evaporated under reduced pressure. The residue obtained is treated with chloroform and 1 N sodium hydroxide solution to remove 1,3-di-n-butyl-xanthine. From the chloroform phase there is obtained a yellow oily residue which after column chromatography on silica gel with methylene chloride/acetone (8:2) as eluent and after distillation under reduced pressure yields 29.7 g (78.8% of theory relative to reacted 1,3-di-n-butyl-xanthine) of the title compound with a melting point of 41° to 42° C.

20: 3-Methyl-7-(but-3-enyl)-xanthine 41.5 g of 3-methyl-xanthine are added with stirring at 70° C. to a solution of 10.2 g of NaOH in 400 ml of methanol/water (1:1). After mixing with 35.1 g of 4-bromobut-1-ene the mixture is stirred under a nitrogen atmosphere for 27 hours at 70° C. The reaction mixture is then cooled to 20° C. and the precipitate formed is filtered off. By re-precipitation from alkaline solution (pH 13.5) and acidification with dilute sulphuric acid to pH 10, 29.6 g (89.7% of theory relative to reacted 3-methyl-xanthine) of the title compound of melting point 245° to 246° C. are obtained after drying.

21: 3-Methyl-7-(pent-4-enyl)-xanthine is prepared analogously to Example 1.

22 to 24: 3-Methyl-7-(hex-5-enyl)-xanthine, 3-ethyl-7-(but-3-enyl)-xanthine and 3-ethyl-7-(hex-5-enyl)-xanthine are prepared analogously to Example 20 from the corresponding alkylxanthines.

25: 1,7-Dimethyl-3-(hex-5-enyl)-xanthine is prepared analogously to Example 6 from 1,7-dimethyl-xanthine and 6-bromo-hex-1-ene.

26: 1,7-Di-(but-3-enyl)-3-ethyl-xanthine is prepared analogously to Example 12 from
(a) 1 mol of 3-ethyl-7-(but-3-enyl)-xanthine and 1 mol of 4-bromo-but-1-ene (yield: 83% of theory relative to reacted 3-ethyl-7-(but-3-enyl)-xanthine); and
(b) 1 mol of 3-ethyl-xanthine and 2 mol of 4-bromo-but-1-ene (yield: 39% of theory relative to reacted 3-ethyl-xanthine).

27: 1-(But-3-enyl)-3-ethyl-7-(hex-5-enyl)-xanthine is prepared analogously to Example 12 from 3-ethyl-7-(hex-5-enyl)-xanthine and 4-bromobut-1-ene (yield: 71.6% of theory relative to reacted 3-ethyl-7-(hex-5-enyl)-xanthine).

28: 1-Hexyl-3-methyl-7-(hex-5-enyl)-xanthine is prepared analogously to Example 1.

29: 1,3-Dimethyl-7-(5-methyl-hex-5-enyl)-xanthine 0.5 g of sodium hydride are reacted with 15 ml of anhydrous dimethyl-sulphoxide under a nitrogen atmosphere with stirring at 80° C. and cooled to 15° C. after 25 minutes. To prepare triphenyl-methylene-phosphorane, 8.1 g of methyl-triphenyl phosphonium iodide in 20 ml of anhydrous dimethyl-sulphoxide are added to this solution. After stirring for 10 minutes at room temperature, 5.6 g of 1,3-dimethyl-7-(5-oxohexyl)-xanthine in 10 ml of dimethylsulphoxide are added dropwise over 10 minutes, and the temperature is not allowed to exceed 20° C. After standing overnight, the mixture is dissolved in water, extracted with diethyl ether and the ether phase is separated and dried over $Na_2SO_4$. The product obtained after evaporation at reduced pressure is subsequently subjected to a purification by column chromatography on silica gel with methylene chloride/acetone (1:1) as eluent. The resulting product is in the form of an oil after distillation under reduced pressure. Yield: 3.5 g (63.3% of theory relative to the starting product used); refractive index: $n_D^{20} = 1.5445$.

30: 1,3-Dimethyl-7-(hex-4-enyl)-xanthine 7 g of 1,3-dimethyl-7-(5-hydroxyhexyl)-xanthine and 9.5 g of p-toluene sulphonic acid are refluxed in 100 ml of toluene for 12 hours with continuous separation of the water formed in the reaction. After cooling to room temperature, the reaction mixture is mixed with 100 ml of diethyl ether, washed with sodium bicarbonate solution and water until neutral and the organic phase dried over sodium sulphate is evaporated under reduced pressure. After column chromatography on silica gel with methylene chloride/acetone (1:1) as eluent and distillation under reduced pressure a product is obtained from the residue which still contains a few percent of isomeric 1,3-dimethyl-7-(hex-5-enyl)-xanthine (as shown by the n.m.r. spectrum). Yield: 4.3 g (65.5% of theory relative to the starting product used). Melting point: 58°–64° C.

31: 1-(Hex-5-enyl)-3,7-dimethyl-xanthine is prepared analogously to example 1.

32 and 33: 1-(Hex-5-enyl)-3-ethyl-7-methyl-xanthine and 1-(Pent-4-enyl)-3-ethyl-7-methyl-xanthine are prepared analogously to Example 12.

34: 1,3-Dimethyl-7-(2-methyl-pent-2-enyl)-xanthine is prepared analogously to Example 29.

35 to 37: The following compounds are prepared analogously to example 6:
1,3-Di-n-propyl-7-(3'-butenyl)-xanthine and 1,3-Di-n-propyl-7-(4'-pentenyl)-xanthine, each identified by NMR-spectrum; 1-Ethyl-3-n-butyl-7-(4'-pentenyl)-xanthine.

38: Preparation of coated tablets 1000 coated tablets are prepared by mixing 100 g of 1,3-dimethyl-7-(hex-5-enyl)-xanthine, 20 g of lactose, 30 g of maize starch, 8.5 g of talcum, 0.5 g of colloidal silica and 1 g of magnesium stearate and compressing to tablet cores of 160 mg weight each. The cores are then coated with a mixture of 44.57 g of cane sugar, 23.4 g of talcum, 8 g of cellulose acetatephthalate, 2.24 g of caster oil and very small quantities of wax, titanium dioxide and gum arabic. The final weight of each coated tablet is 240 mg. It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

Table 2

| Ex. | compound 1- | 3- | 7-position | mp °C. | recry. from | b.p. C/mbar | Rf | $n_D^{20}$ | yield | sum formula mol weight | analysis | | | calc: found: |
|---|---|---|---|---|---|---|---|---|---|---|---|---|---|---|
| 1 | $CH_3$ | $CH_3$ | but-3-enyl | 110 | acetone | | (1)0,54 (2)0,65 | | 91% | $C_{11}H_{14}N_4O_2$ 234,3 | C 56,4 C 56,3 | H 6,0 H 6,0 | N 23,9 N 23,8 | |
| 2 | $CH_3$ | $CH_3$ | pent-4-enyl | 92 | hexane | | (1)0,66 (2)0,52 | | 92% | $C_{12}H_{16}N_4O_2$ 248,3 | C 58,1 C 58,1 | H 6,5 H 6,3 | N 22,6 N 22,7 | |
| 3 | $CH_3$ | $CH_3$ | hex-5-enyl | 42 | hexane | | (1)0,61 (2)0,67 | | 94% | $C_{13}H_{18}N_4O_2$ 262,3 | C 59,5 C 59,4 | H 6,9 H 6,9 | N 21,4 N 21,6 | |
| 4 | but-3-enyl | $CH_3$ | $CH_3$ | 115 | acetone | | (1)0,52 (2)0.50 | | 93% | $C_{11}H_{14}N_4O_2$ 234,3 | C 56,4 C 56,5 | H 6,0 H 5,9 | N 23,9 N 24,0 | |

Table 2-continued

| Ex. | compound 1- | 3- | 7-position | mp °C. | recry. from | b.p. C/mbar | Rf | $n_D^{20}$ | yield | sum formula mol weight | analysis | calc: found: |
|---|---|---|---|---|---|---|---|---|---|---|---|---|
| 5 | pent-4-enyl | $CH_3$ | $CH_3$ | 94 | hexane | | (1)0,54 (2)0,46 | | 91% | $C_{12}H_{16}N_4O_2$ 248,3 | C 58,1 C 58,1 | H 6,5 N 22,6 H 6,6 N 22,6 |
| 6 | but-3-enyl | $CH_3$ | propyl | 48 | hexane | | (4)0,77 | | 70% | $C_{13}H_{18}N_4O_2$ 262,3 | C 59,5 C 59,7 | H 6,9 N 21,4 H 7,0 N 21,3 |
| 7 | but-3-enyl | $CH_3$ | hexyl | | | 190/1,1 | (4)0,68 | 1,5310 | 80% | $C_{16}H_{24}N_4O_2$ 304,4 | C 63,1 C 63,0 | H 7,9 N 18,4 H 8,1 N 18,5 |
| 8 | hex-5-enyl | $CH_3$ | propyl | 43 | (++) | | (4)0,67 | | 81% | $C_{15}H_{22}N_4O_2$ 290,4 | C 62,0 C 62,2 | H 7,6 N 19,3 H 7,8 N 19,7 |
| 9 | hex-5-enyl | $CH_3$ | hexyl | | | 195/0,33 | (4)0,82 | 1,5265 | 75% | $C_{18}H_{28}N_4O_2$ 332,5 | C 65,0 C 64,7 | H 8,5 N 16,9 H 8,6 N 17,1 |
| 10 | hex-5-enyl | $CH_3$ | decyl | 39 | (++) | | (4)0,87 | | 69% | $C_{22}H_{36}N_4O_2$ 388,6 | C 68,0 C 68,3 | H 9,3 N 14,4 H 9,5 N 14,5 |
| 11 | $C_2H_5$ | $CH_3$ | hex-5-enyl | | | | (3)0,71 | 1,5415 | 81% | $C_{14}H_{20}N_4O_2$ 276,3 | C 60,9 C 60,6 | H 7,3 N 20,3 H 7,4 N 20,2 |
| 12 | Propyl | $CH_3$ | but-3-enyl | 55–56 | | | | | 71% | $C_{13}H_{18}N_4O_2$ 262,3 | C 59,5 C 59,6 | H 6,9 N 21,4 H 7,1 N 21,6 |
| 13 | Hexyl | $CH_3$ | but-3-enyl | (+)92 | di-ethyl-ether | | (1)0,54 (2)0,58 | | 89% | $C_{16}H_{25}ClN_4O_2$ 340,9 | C 56,4 C 56,5 | H 7,4 Cl 10,4 N 16,4 H 7,3 Cl 10,4 N 16,6 |
| 14 | Hexyl | $CH_3$ | pent-4-enyl | (+)98 | di-ethyl-ether | | (1)0,54 (2)0,61 | | 92% | $C_{17}H_{27}ClN_4O_2$ 354,9 | C 57,5 C 57,6 | H 7,7 Cl 10,0 N 15,8 H 7,7 Cl 10,2 N 15,7 |
| 15 | Decyl | $CH_3$ | but-3-enyl | 74 | white spirit | | | | 82% | $C_{20}H_{32}N_4O_2$ 360,5 | C 66,6 C 66,5 | H 9,0 N 15,5 H 9,0 N 15,3 |
| 16 | $CH_3$ | $C_2H_5$ | hex-5-enyl | | | | (3)0,81 | 1,5400 | 89% | $C_{14}H_{20}N_4O_2$ 276,3 | C 60,8 C 60,6 | H 7,3 N 20,3 H 7,4 N 20,5 |
| 17 | $C_2H_5$ | $C_2H_5$ | pent-4-enyl | | | | (3)0,9 | 1,5384 | 84% | $C_{14}H_{20}N_4O_2$ 276,3 | C 60,8 C 60,8 | H 7,3 N 20,3 H 7,4 N 20,3 |
| 18 | $C_2H_5$ | $C_2H_5$ | hex-5-enyl | | | | (3)0,94 | 1,5345 | 79% | $C_{15}H_{22}N_4O_2$ 290,4 | C 62,1 C 61,8 | H 7,6 N 19,3 H 7,7 N 19,0 |
| 19 | Butyl | butyl | but-3-enyl | 41–42 | | | | | 79% | $C_{17}H_{26}N_4O_2$ 318,4 | C 64,1 C 63,9 | H 8,2 N 17,6 H 8,1 N 17,5 |
| 20 | H | $CH_3$ | but-3-enyl | 245–246 | | | | | 90% | $C_{10}H_{12}N_4O_2$ 220,2 | C 54,5 C 54,3 | H 5,5 N 25,4 H 5,4 N 25,4 |
| 21 | H | $CH_3$ | pent-4-enyl | 202 | methanol/ $H_2O$ | | (1)0,50 (2)0,27 | | 87% | $C_{11}H_{14}N_4O_2$ 234,3 | C 56,4 C 56,5 | H 6,0 N 23,9 H 5,9 N 23,8 |
| 22 | H | $CH_3$ | hex-5-enyl | 206 | | | | | 83% | $C_{12}H_{16}N_4O_2$ 248,3 | C 58,1 C 57,9 | H 6,5 N 22,6 H 6,6 N 22,5 |
| 23 | H | $C_2H_5$ | but-3-enyl | 146–147 | | | | | 81% | $C_{11}H_{14}N_4O_2$ 234,3 | C 56,4 C 56,2 | H 6,0 N 23,9 H 6,0 N 24,1 |
| 24 | H | $C_2H_5$ | hex-5-enyl | 130 | | | | | 85% | $C_{13}H_{18}N_4O_2$ 262,3 | C 59,5 C 59,6 | H 6,9 N 21,4 H 6,9 N 21,6 |
| 25 | $CH_3$hex-5-enyl | | $CH_3$ | 69–70 | (++) | | | | 75% | $C_{13}H_{18}N_4O_2$ 262,3 | C 59,5 C 59,6 | H 6,9 N 21,4 H 6,9 N 21,3 |
| 26 | but-3-enyl $C_2H_5$ | | but-3-enyl | 63 | | | | | (a) 83% (b) 39% | $C_{15}H_{20}N_4O_2$ 288,4 | C 62,5 C 62,7 | H 7,0 N 19,4 H 7,1 N 19,5 |
| 27 | but-3-enyl $C_2H_5$ | | hex-5-enyl | | | | (3)1,0 | 1,5350 | 72% | $C_{17}H_{24}N_4O_2$ 316,4 | C 64,5 C 64,6 | H 7,7 N 17,7 H 7,8 N 17,9 |
| 28 | Hexyl | $CH_3$ | hex-5-enyl | | | 193/0,4 | | | 92% | $C_{18}H_{28}N_4O_2$ 332,5 | C 65,0 C 64,7 | H 8,5 N 16,9 H 8,2 N 16,9 |
| 29 | $CH_3$ | $CH_3$ | 5-$CH_3$-hex-5-enyl | | | | | 1,5445 | 63% | $C_{14}H_{20}N_4O_2$ 276,3 | C 60,8 C 60,9 | H 7,3 N 20,3 H 7,3 N 20,3 |
| 30 | $CH_3$ | $CH_3$ | hex-4-enyl | 58–64 | | | | | 65% | $C_{13}H_{18}N_4O_2$ 262,3 | C 59,5 C 59,6 | H 6,9 N 21,4 H 7,1 N 21,5 |
| 31 | hex-5-enyl | $CH_3$ | $CH_3$ | 76–77 | hexane | | (1)0,47 (2)0,60 | | 92% | $C_{13}H_{18}N_4O_2$ 262,3 | C 59,5 C 59,6 | H 6,9 N 21,4 H 7,1 N 21,2 |
| 32 | hex-5-enyl | $C_2H_5$ | $CH_3$ | 64 | | | | | 75% | $C_{14}H_{20}N_4O_2$ 276.3 | C 60,9 C 60,6 | H 7,3 N 20,3 H 7,2 N 20,2 |
| 33 | pent-4-enyl | $C_2H_5$ | $CH_3$ | | | | | 1,5460 | 78% | $C_{13}H_{18}N_4O_2$ 262,3 | C 59,5 C 59,4 | H 6,9 N 21,4 H 7,0 N 21,4 |
| 34 | $CH_3$ | $CH_3$ | 2-$CH_3$-pent-2-enyl | 104–106 | (++) | | | | 55% | $C_{13}H_{18}N_4O_2$ 262,3 | C 59,5 C 59,6 | H 6,9 N 21,4 H 7,0 N 21,6 |
| 35 | Propyl | propyl | 3'-butenyl | | | | | | | | | |
| 36 | Propyl | propyl | 4'-pentenyl | | | | | | | | | |
| 37 | Ethyl | n-butyl | 4'-pentenyl | | | | | 1,5304 | | $C_{16}H_{24}N_4O_2$ | C 63,1 | H 7,9 N 18,4 |

Table 2-continued

| Ex. | compound 1- | 3- | 7-position | mp °C. | recry. from | b.p. C/mbar | Rf | $n_D^{20}$ | yield | sum formula mol weight | analysis | calc: found: |
|---|---|---|---|---|---|---|---|---|---|---|---|---|
| | | | | | | | | | | | | C 63,1 H 8,1 N 18,2 |

Remarks:
(+) = values as hydrochloride
(++) = diisopropyl ether
eluent: thin-layer chromatography
(1) = benzene/acetone (6:4)
(2) = nitromethane/Benzene/pyridine (20:10:3)
(3) = toluene/acetone (7:3) (all values in relation to example 27 = 1.0)
(4) = chloroform/benzene/acetone (1:1:1)

What we claim is:

1. A blood-perfusion-promoting pharmaceutical composition comprising pharmacologically-acceptable excipient and, as a single essential active ingredient, an effective amount of a compound of the formula

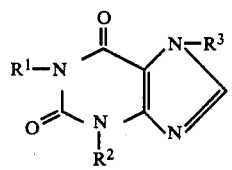

wherein
$R^1$ is —H or one of the meanings of $R^2$;
$R^2$ is alkenyl having from 4 to 8 carbon atoms or alkyl having from 1 to 12 carbon atoms; and
$R^3$ is one of the meanings of $R^2$; at least one of $R^1$, $R^2$ and $R^3$ being alkenyl.

2. A composition as claimed in claim 1, wherein at least one of the alkenyl groups is an (ω-1)-alkenyl.

3. A composition as claimed in claim 1, containing a compound of formula I wherein one of the groups $R^1$, $R^2$ and $R^3$ is an (ω-1)-alkenyl, the C-atom bearing the double bond being separated from the xanthine nucleus by at least one saturated carbon atom, and the other two are methyl or $R^1$ is hydrogen, $R^2$, however, always being methyl or alkenyl.

4. A composition as claimed in claim 3, containing a compound of formula I, wherein one of the groups $R^1$ and $R^3$ is a straight-chained (ω-1)-alkenyl, having from 4 to 8 carbon atoms and the other one is methyl.

5. A composition as claimed in claim 3, wherein the alkenyl group has 5 to 8 carbon atoms.

6. A composition as claimed in claim 1 wherein the alkenyl is an (ω-1) alkenyl having a chain of at least 4 carbon atoms.

7. A substantially non-toxic pharmaceutical composition according to claim 1 for increasing blood perfusion comprising carrier, diluent or excipient in addition to an effective concentration of active ingredient which consists essentially of substituted xanthine of formula I wherein each of $R^1$, $R^2$ and $R^3$ has one of the meanings ascribed to it in claim 1.

8. A composition as claimed in claim 1, wherein only one of $R^1$, $R^2$ and $R^3$ is an alkyl having at most 2 carbon atoms and the other ones are alkenyl, alkyl having at least 3 carbon atoms or wherein $R^1$ is hydrogen.

9. A composition of claim 1 wherein each of from 1 to 3 of $R^1$, $R^2$ and $R^3$ is alkenyl having from 4 to 8 carbon atoms; $R^1$ is —H, alkyl having from 1 to 12 carbon atoms or such alkenyl; and $R^2$ and $R^3$ each are alkyl having from 1 to 12 carbon atoms or such alkenyl; with the proviso that $R^1$ is not but-3-enyl, pent-4-enyl, hex-5-enyl or 2-methyl-but-3-enyl when each of $R^2$ and $R^3$ is methyl; $R^1$ is not hex-5-enyl when $R^2$ is methyl and $R^3$ is ethyl, propyl, butyl, isobutyl, decyl or hex-5-enyl; $R^3$ is not 2-methyl-but-3-enyl, but-3-enyl, pent-4-enyl, hex-5-enyl or hept-6-enyl when each of $R^1$ and $R^2$ is methyl; and $R^3$ is not hex-5-enyl when $R^2$ is methyl and $R^1$ is —H, propyl, isobutyl, pentyl or hexyl.

10. A composition as defined in claim 1, wherein one to three of $R^1$, $R^2$ and $R^3$ represent an alkenyl group having from 4 to 8 carbon atoms, the other are alkyl having from 1 to 12 carbon atoms, and $R^1$ may also be hydrogen and wherein, if $R^2$ is methyl and $R^1$ or $R^3$ is an (ω-1)-alkenyl being unbranched in (ω-1)-position, the sum of the carbon atoms of the alkyls $R^1$ and $R^2$ is more than 7 and the sum of the carbon atoms of the alkyls $R^2$ and $R^3$ is more than 11.

11. A composition as defined in claim 1, wherein at least one of $R^1$, $R^2$ and $R^3$ is alkyl having from 3 to 12 carbon atoms and at least one is butenyl or pentenyl, $R^1$ is such alkyl, alkenyl or hydrogen and one of $R^1$, $R^2$ and $R^3$ is also optionally methyl or ethyl.

12. A composition as defined in claim 1, wherein more than one of the radicals $R^1$, $R^2$ and $R^3$ is alkenyl.

13. A composition as defined in claim 1, wherein the alkenyl is a hexenyl and the double bond is in a position other than (ω-1).

14. A composition as defined in claim 1, wherein $R^2$ is alkyl having from 2 to 12 carbon atoms or alkenyl having from 4 to 8 carbon atoms and wherein only one of $R^1$, $R^2$ and $R^3$ is alkyl having at most 2 carbon atoms and the other ones are alkenyl, alkyl having at least three carbon atoms or $R^1$ optionally is hydrogen.

15. A composition as defined in claim 1, wherein $R^1$ is hydrogen, $R^2$ is alkyl having from 1 to 12 carbon atoms and $R^3$ is butenyl or pentenyl.

16. A composition as defined in claim 1, wherein the alkenyl is branched and has a chain length of at least 4 carbon atoms.

17. A composition as defined in claim 1, wherein $R^1$ is ethyl, $R^2$ is methyl or ethyl and $R^3$ is alkenyl.

18. A composition as defined in claim 1, wherein $R^1$ is alkenyl, $R^2$ is methyl and $R^3$ is hexyl.

19. A composition as defined in claim 1, wherein $R^1$ is alkyl having from 2 to 12 carbon atoms or alkenyl, $R^2$ is alkyl having from 2 to 12 carbon atoms and $R^3$ is alkyl having from 1 to 12 carbon atoms or alkenyl with the proviso that one of the groups $R^1$ and $R^3$ is alkenyl, at least one of the groups $R^1$ and $R^2$ have at least 3 carbon atoms and all of $R^1$, $R^2$ and $R^3$ have not the same number of carbon atoms.

20. A composition according to claim 1 having from 10 to 1,000 mg of the compound of formula (I) per dosage unit.

21. A composition according to claim 20 in dosage-unit form and having up to 400 mg of the compound of formula (I) per dosage unit.

* * * * *